(12) United States Patent
Razzetti et al.

(10) Patent No.: US 7,291,742 B2
(45) Date of Patent: Nov. 6, 2007

(54) PROCESS FOR THE PREPARATION OF BENZO [D] ISOXAZOL-3-YL-METHANESULFONIC ACID AND THE INTERMEDIATES THEREOF

(75) Inventors: Gabriele Razzetti, Sesto S. Giovanni (IT); Simone Mantegazza, Milan (IT); Graziano Castaldi, Briona (IT); Plietro Allegrini, San Donato Milanese (IT); Vittorio Lucchini, San Donato Milanese (IT); Alberto Bologna, Crema (IT)

(73) Assignee: Dipharma S.p.A., Mereto di Tomba (IT)

( * ) Notice: Subject to any disclaimer, the term of this patent is extended or adjusted under 35 U.S.C. 154(b) by 224 days.

(21) Appl. No.: 10/541,607

(22) PCT Filed: Dec. 24, 2003

(86) PCT No.: PCT/EP03/14919

§ 371 (c)(1),
(2), (4) Date: Jul. 7, 2005

(87) PCT Pub. No.: WO2004/063173

PCT Pub. Date: Jul. 29, 2004

(65) Prior Publication Data

US 2006/0135582 A1    Jun. 22, 2006

(30) Foreign Application Priority Data

Jan. 10, 2003  (IT)  .......................... MI2003A0026
Jul. 4, 2003   (IT)  .......................... MI2003A1383

(51) Int. Cl.
*C07D 339/08*    (2006.01)
*C07D 261/20*    (2006.01)
(52) U.S. Cl. .......................................... 548/241; 549/15
(58) Field of Classification Search ................ 548/241; 549/15
See application file for complete search history.

(56) References Cited

U.S. PATENT DOCUMENTS 4,172,896 A    10/1979    Uno et al.

FOREIGN PATENT DOCUMENTS

| WO | WO 02/070495 | 9/2002 |
| WO | WO 03/040096 | 5/2003 |
| WO | WO 03/072552 | 9/2003 |

OTHER PUBLICATIONS

Patent Abstracts of Japan, vol. 0021, No. 10 (C-022), Sep. 13, 1978 -& JP-53 077057 A (Dainippon Pharmaceut Co Ltd), Jul. 8, 1978 cited in the application scheme p. 443.
Database Caplus Online !, Chemical Abstracts Service, Columbus, Ohio, US;, Uno, Hitoshi et al:, "Studies on 3-substituted 1,2-benziasoxazole derivatives. VII. Catalytic reduction of 3-sulfamoylmethyl-1,2-benzisoxazole and reactions of the resulting products", XP002284802, retrieved from STN, Database accession No. 1982: 181246, RN 81534-20-5, abstract & Chemical & Pharmaceutical Bulletin, 30(1), 333-5 CODEN: CPBTAL; ISSN: 0009-2363, 1982.

*Primary Examiner*—Kamal A. Saeed
(74) *Attorney, Agent, or Firm*—Young & Thompson

(57) ABSTRACT

A process for the preparation of benzo[d]isoxazol-3-yl-methanesulfonic acid of formula (I), or a salt thereof, and the intermediates thereof, useful as an intermediate in the preparation of zonisamide.

8 Claims, No Drawings

PROCESS FOR THE PREPARATION OF BENZO [D] ISOXAZOL-3-YL-METHANESULFONIC ACID AND THE INTERMEDIATES THEREOF

The present invention relates to a process for the preparation of benzo[d]isoxazol-3-yl-methanesulfonic acid or a salt thereof, useful as an intermediate for the preparation of zonisamide, and intermediates thereof.

TECHNOLOGICAL BACKGROUND

Zonisamide, namely 3-(sulfamylmethyl)-benzo[d]isoxazole, is a known medicament having antiepileptic, anticonvulsive and antineurotoxic activities, belonging to the class of the sulfonamides, and having the following formula:

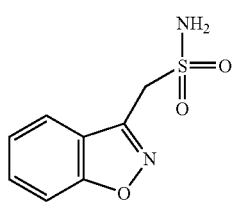

A process for the preparation of zonisamide, disclosed in U.S. Pat. No. 4,172,896, comprises the sulfonation of 3-bromomethyl-benzo[d]isoxazole (1) with sodium sulfite to obtain benzo[d]isoxazol-3-yl-methanesulfonic acid sodium salt (2) which is then transformed into the corresponding sulfonyl chloride (3) by treatment with phosphorous oxychloride. The reaction of the latter with gas ammonia yields zonisamide (4), as reported hereinbelow.

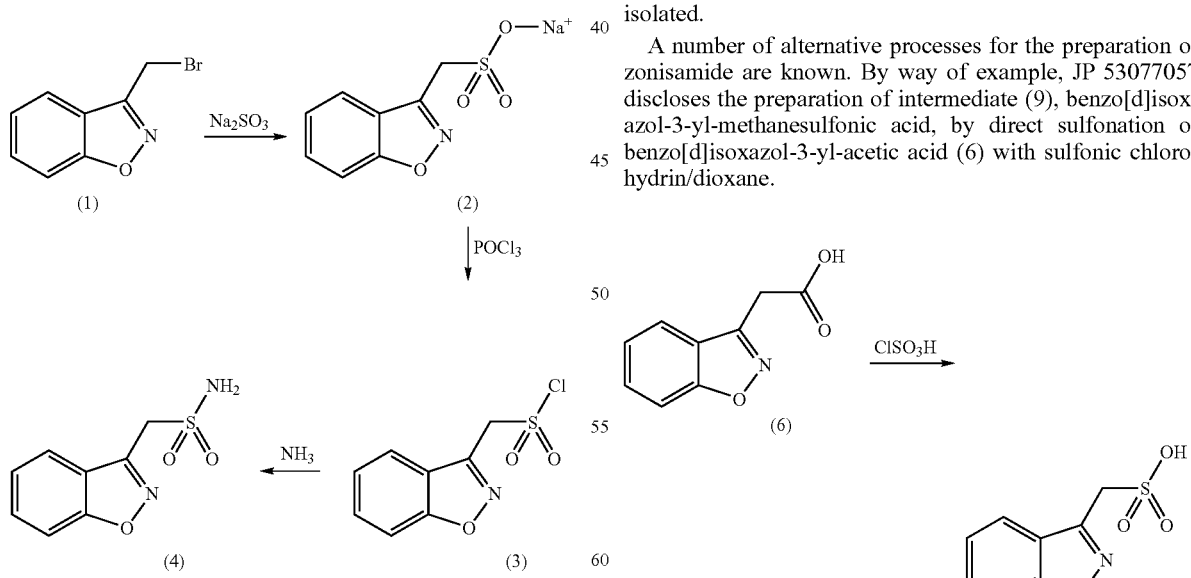

The starting compound (1) is not commercially available. Its preparation is described in BE 624463; Chem. Pharm. Bull. 24 (1976) p. 632; and Chim. Ter. 7 (1972) p. 127 starting from 4-hydroxycoumarin (5), according to the following scheme:

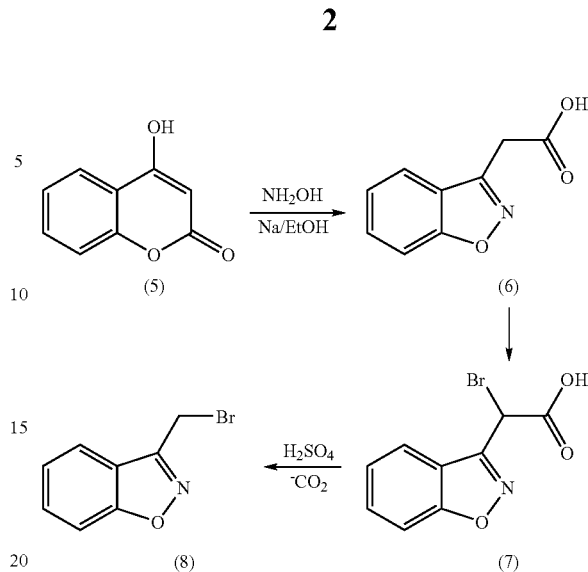

Hydroxycoumarin (5) is treated with hydroxylamine to obtain benzo[d]isoxazol-3-yl-acetic acid (6) which is brominated at the alpha position to give benzo[d]isoxazol-3-yl-bromoacetic acid (7) from which 3-bromomethyl-benzo[d]isoxazole (8) is obtained by decarboxylation. The development of this process is limited in that the starting intermediate (1) is not commercially available and therefore the preparation of zonisamide is very complex. In fact, Posner reaction for the preparation of acid (6) requires the use of metal sodium. Moreover, when metal sodium is used in alcoholic solution, besides acid (6) also remarkable amounts of O-hydroxy-acetophenone-oxime as by-product are obtained. Furthermore, the decarboxylation reaction to give compound (8) requires drastic conditions, namely the presence of a large excess of 50% sulfuric acid and reflux temperature, and the resulting product is thus difficult to be isolated.

A number of alternative processes for the preparation of zonisamide are known. By way of example, JP 53077057 discloses the preparation of intermediate (9), benzo[d]isoxazol-3-yl-methanesulfonic acid, by direct sulfonation of benzo[d]isoxazol-3-yl-acetic acid (6) with sulfonic chlorohydrin/dioxane.

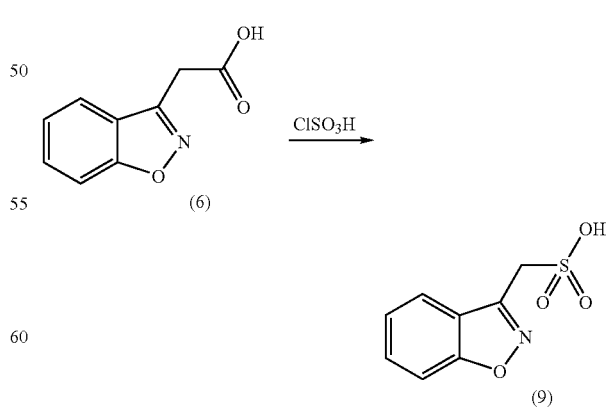

The use of sulfonic chlorohydrin and dioxane is disadvantageous, as these products are highly toxic and difficult to handle.

JP 54163510 describes the synthesis of zonisamide (4) starting from 2-(2-hydroxy-phenyl)-2-oxo-ethanesulfonamide (10) by formation of the corresponding 2-hydroxyimmino-2-(2-hydroxy-phenyl)ethanesulfonamide (11) and subsequent thermal cyclization.

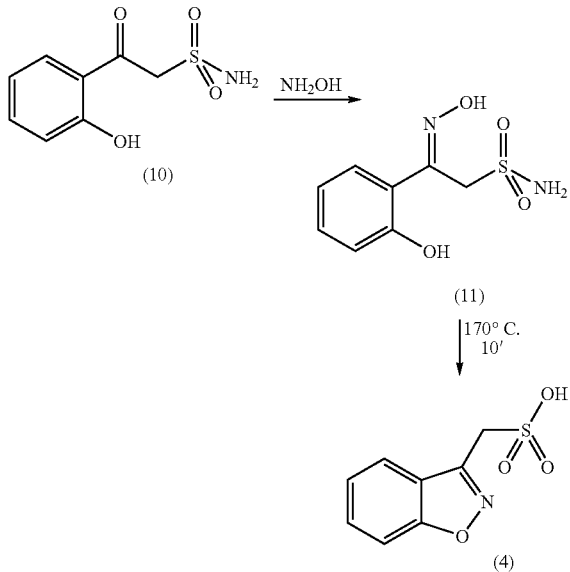

The main drawbacks of this synthetic route are that the starting product (10) is not commercially available and the yield is low (approx. 6%, calculated on the last step). There is therefore the need for an alternative method which allows to prepare zonisamide in highly pure form and good yield, suitable for the preparation on an industrial scale.

DETAILED DISCLOSURE OF THE INVENTION

The present invention relates to a process for the preparation of benzo[d]isoxazol-3-yl-methanesulfonic acid of formula (I), or a salt thereof,

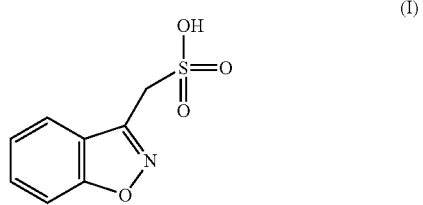

comprising the reaction of an oxime of formula (III)

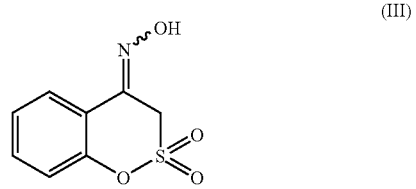

with a basic agent.

Suitable benzo[d]isoxazol-3-yl-methanesulfonic acid salts of formula (I) are, for example, the alkali or alkaline-earth salts, in particular the sodium, potassium, lithium, calcium or barium, preferably sodium or lithium, salts; or the salts with organic bases, for example with a secondary or tertiary amine, typically triethylamine, tributylamine, diisopropylethylamine, dicyclohexylamine, 1,4-diazabicyclo[2,2,2]octane, 1,8-diazabicyclo[5,4,0]-undec-4-ene or 1,5-diazabicyclo[4,3,0]non-5-ene, preferably triethylamine or 1,8-diazabicyclo[5,4,0]undec-4-ene.

The invention also relates to both the benzo[d]isoxazol-3-yl-methanesulfonic acid lithium salt and the salts of benzo[d]isoxazol-3-yl-methanesulfonic acid with organic bases, for example with a secondary or tertiary amine, typically triethylamine, tributylamine, diisopropylethylamine, dicyclohexylamine, 1,4-diazabicyclo[2,2,2]octane, 1,8-diazabicyclo[5,4,0]-undec-4-ene or 1,5-diazabicyclo[4,3,0]non-5-ene, preferably triethylamine or 1,8-diazabicyclo-[5,4,0]undec-4-ene, which are novel compounds.

The oxime of formula (III) spontaneously transforms into the corresponding benzo[d]isoxazol-3-yl-methanesulfonic acid salt of formula (I) by treatment with a basic agent. The basic agent is preferably a hydroxide of an alkali or alkaline-earth metal, for example lithium, sodium, potassium, calcium or magnesium, in particular lithium or sodium, or an organic base, for example a secondary or tertiary amine, typically triethylamine, tributylamine, diisopropylethylamine, dicyclohexylamine, 1,4-diazabicyclo[2,2,2]octane, 1,8-diazabicyclo-[5,4,0]undec-4-ene or 1,5-diazabicyclo[4,3,0]non-5-ene, preferably triethylamine or 1,8-diazabicyclo[5,4,0]undec-4-ene.

The basic agent can be used in a reaction ratio from approx. one to two equivalents with respect to the amount of oxime, preferably in a stoichiometric amount.

The transformation reaction can be carried out, depending on the base, in the absence or in the presence of a solvent selected, for example, from the group consisting of water; ethers, in particular tetrahydrofuran; $C_1$-$C_4$ alkanols, particularly methanol or ethanol; acetonitrile; chlorinated solvents, such as dichloromethane, dichloroethane or trichloroethane; carboxylic acids alkyl esters, such as ethyl acetate; apolar aprotic solvents, such as toluene or cyclohexane; or mixtures thereof, such as tetrahydrofuran/water, acetonitrile/water, ethyl acetate/methanol or acetonitrile/methanol. The reaction is preferably carried out in water, acetonitrile/methanol or dichloromethane. The reaction is preferably carried out at a temperature ranging, from about −20° C. to the reflux temperature of the solvent or solvent mixture, in particular at temperatures approx. ranging from 30 to 50° C. The resulting salt of a compound of formula (I) can be recovered directly or, if desired, can be converted into the free acid with known methods. The process of the invention allows to obtain benzo[d]isoxazol-3-yl-methanesulfonic salt, or a salt thereof, with less environmental impact, in purer form and higher yields than with the method disclosed in U.S. Pat. No. 4,172,896. This particularly applies when oxime of formula (III) is treated with lithium or sodium hydroxide, triethylamine or diazabicycloundecene. Treatment with these specific basic agents allows, in fact, to obtain benzo[d]isoxazol-3-yl-methanesulfonic acid in purer form and higher yields than when using other basic agents.

An oxime of formula (III) and the isomers thereof can be obtained by reaction of a ketosultone of formula (II)

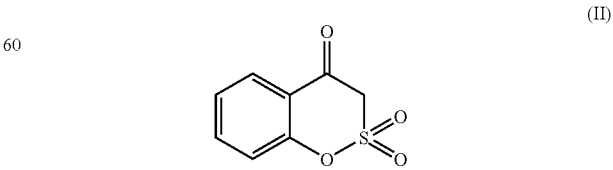

with hydroxylamine, at a temperature ranging from about 5 to about 100° C., preferably at temperatures ranging from about 15 to about 40° C. The reaction is carried out in water, in an organic solvent or in mixtures thereof. The organic solvent can be an organic protic solvent, such as a $C_1$-$C_6$ alkanol, in particular methanol, ethanol or isopropanol; a halo hydrocarbon, such as chloroform or dichloromethane; an aromatic hydrocarbon, such as benzene or toluene; an ether, such as diethyl ether or tetrahydrofuran; or a carboxylic acid alkyl ester, such as ethyl acetate.

Hydroxylamine can be used as an aqueous solution, or can be obtained in situ in the reaction medium from a salt thereof, for example sulfate, nitrate or chloride, by reaction with a suitable basic agent, such as sodium hydroxide, sodium carbonate or organic bases, such as triethylamine. The resulting oxime of formula (III), if desired, can be crystallized for instance from $C_1$-$C_4$ alkanols in particular isopropanol, $C_1$-$C_4$ alkanols aqueous mixtures in particular isopropanol/water, toluene or dichloromethane/water mixtures. A crystalline oxime of formula (III), and the isomers thereof, in particular having the tabulation of peak position from X-Ray Powder pattern listed in Table 1, is novel and is a further object of the invention.

TABLE 1

X-Ray Powder Diffraction Significant Peaks

| Nr. | 2-Theta (degrees) ±0.1 | d(Å) | I/Imax (%) |
|---|---|---|---|
| 1 | 8.5 | 10.37 | 21 |
| 2 | 11.2 | 7.87 | 6 |
| 3 | 16.4 | 5.40 | 17 |
| 4 | 17.2 | 5.15 | 100 |
| 5 | 20.1 | 4.41 | 7 |
| 6 | 22.5 | 3.94 | 12 |
| 7 | 23.7 | 3.74 | 7 |
| 8 | 24.3 | 3.65 | 5 |
| 9 | 26.0 | 3.42 | 5 |
| 10 | 28.6 | 3.11 | 25 |

Ketosultone of formula (II) is known and can be obtained in small amounts with known, rather inexpensive methods, for example according to *Int. J. Sulfur. Chem.*, Part A, (1992), 2(4), 249-255; or *Arch. Pharm*, 313,1980. p. 249. The synthetic route therein described is the following:

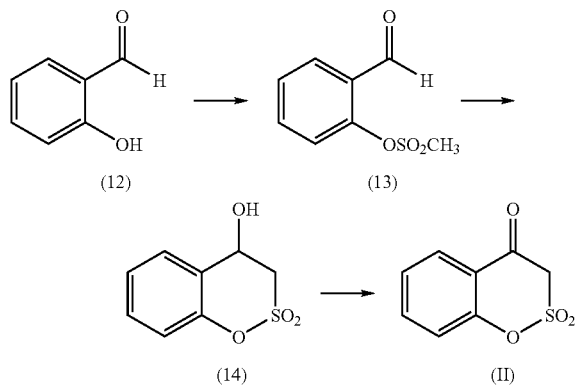

The process comprises the mesylation of salicylaldehyde (12) and the subsequent cyclization of derivative (13) with potassium hydroxide. The resulting compound (14) is oxidized to the desired compound (II) by use of potassium dichromate and sulfuric acid. This procedure cannot however be adopted to obtain ketosultone (II) in industrial amounts, in that it involves the use of potassium dichromate, which is known to be carcinogenic, teratogenic and highly toxic to the environment.

Another synthetic route is known from *Heterocycles*, vol. 22, n° 10,1984, p.2293, in which

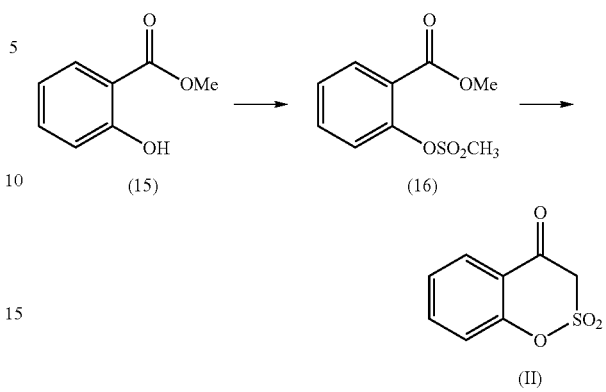

the ring closure is obtained by treatment of methyl salicylate mesylate (16) with sodium hydride in dimethylformamide (DMF). On the other hand, it is known from literature (e.g. *Bretherick's Handbook of reactive chemical hazards*, VI Ed., p1181) that the sodium hydride-DMF mixture is potentially hazardous and easily undergoes uncontrollable, explosive reactions, even at room temperature. Therefore, this procedure can not be used on an industrial scale.

It has now been found that ketosultone of formula (II), i.e. 2,2-dioxo-2,3-dihydro-21ambda*6*-benzo[e][1,2]oxathiin-4-one, can be conveniently prepared on an industrial scale by means of a process comprising the reaction of a compound of formula (V)

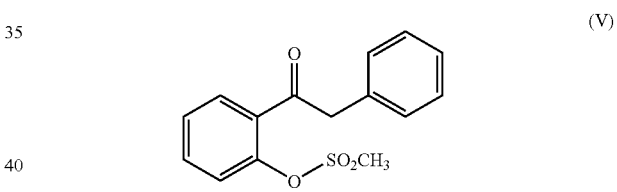

(V)

with a basic agent.

A suitable basic agent is typically an agent selected from the group consisting of an alkali or alkaline-earth metal $C_1$-$C_8$ alkoxide, or a tertiary amine or catalytic amounts thereof.

An alkali or alkaline-earth metal $C_1$-$C_8$ alkoxide can be a sodium or potassium salt with a straight or branched $C_1$-$C_5$ alkanol, typically methanol, ethanol, tert-butanol and isoamyl alcohol, preferably sodium tert-butylate.

The tertiary amine is an amine having such basicity as to induce the conversion of a compound of formula (V) into a ketosultone of formula (II). Examples of such tertiary amines are 1,4-diazabicyclo[2,2,2]octane, 1,8-diazabicyclo [5,4,0]undec-4-ene or 1,5-diazabicyclo[4,3,0]non-5-ene, in particular 1,8-diazabicyclo[5,4,0]undec-4-ene. The molar ratio of tertiary amine to compound of formula (V) can for instance range from about 10/1 to 2/1, preferably approximately from 2.2/1 to 2.1/1.

The reaction between a compound of formula (V) and a basic agent is preferably carried out in an organic solvent selected, for example, from a chlorinated solvent such as $C_1$-$C_4$ alkyl hydrocarbons mono-, di-, tri- and tetra-chlorides, typically dichloromethane, trichloromethane, tetrachloromethane, trichloroethane or tetrachloroethane, in particular dichloroethane; an ether, such as diethyl ether or tetrahydrofuran, preferably tetrahydrofuran; an apolar aprotic solvent, such as pentane, hexane, cyclohexane, benzene, toluene, preferably toluene; a dipolar aprotic solvent, for example dimethylformamide or N-methylpyrrolidone; and acetonitrile. More preferably the solvent is tetrahydrofuran.

Alternatively, the conversion into ketosultone of formula (II) can be obtained by reacting a compound of formula (V) in an organic solvent, as exemplified above, with catalytic amounts of said tertiary amine, for example about 10-20% molar, in the presence of carbonates or hydroxides of alkali or alkaline-earth metals such as lithium, sodium, potassium, calcium, magnesium; preferably potassium carbonate.

The reaction is carried out at a temperature ranging from 0° C. to the reflux temperature of the reaction mixture, preferably from room temperature to 40° C., for times from an hour to 18 hours, depending on the basic agent. A compound of formula (V) can be prepared by acylation of a compound of formula (VI)

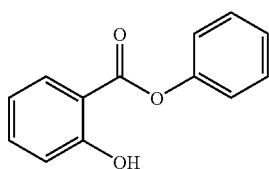

(VI)

with an acylating agent of formula $CH_3SO_2X$, wherein X is halogen, such as chlorine or bromine, preferably chlorine. Acylation of a compound of formula (VI) can be carried out with known methods, for example as illustrated in the following experimental section, in particular in an apolar aprotic solvent as exemplified above.

This process, which is a further object of the invention, allows to prepare ketosultone of formula (II) in yields ranging from 50 to 80%, using intermediates which do not involve hazards to the handler or the environment, while being well-suited to the industrial production. Finally, ketosultone (II) can be easily isolated following work-up with acids.

Ketosultone of formula (II), used in the preparation of benzo[d]isoxazol-3-yl-methanesulfonic acid of formula (I) or a salt thereof, is preferably prepared according to the process of the invention.

The processes of the invention for the preparation of both benzo[d]isoxazol-3-yl-methanesulfonic acid of formula (I), or a salt thereof, and the intermediates of formula (II) and (III), allow to obtain zonisamide at lower costs and higher purity degree than the process disclosed in U.S. Pat. No. 4,172,896.

A further object of the invention is therefore a process for the preparation of zonisamide, comprising the treatment of benzo[d]isoxazol-3-yl-methanesulfonic acid of formula (I), or a salt thereof,

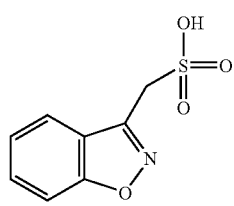

(I)

with an halogenating agent to obtain a benzo[d]isoxazol-3-yl-methanesulfonyl halide of formula (IV)

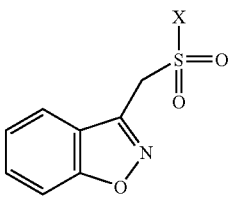

(IV)

wherein X is halogen, preferably chlorine or bromine, and following treatment of (IV) with ammonia; wherein the benzo[d]isoxazol-3-yl-methanesulfonic acid of formula (I), or a salt thereof, is obtained by a process comprising the treatment of an oxime of formula (III) with a basic agent as defined above

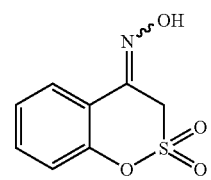

(III)

The basic agent is preferably lithium or sodium hydroxide, triethylamine or diazabicycloundecene. A suitable halogenating agent is for example phosphorous oxychloride or phosphorous oxybromide.

The steps for the conversion of a compound of formula (I), or a salt thereof, into a compound of formula (IV) and then into zonisamide can be carried out as disclosed in U.S. Pat. No. 4,172,896.

According to a preferred aspect of the invention, an oxime of formula (III) and the isomers thereof, if the case in crystalline form,

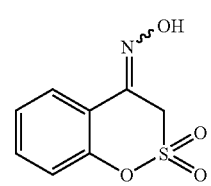

(III)

is prepared by a process comprising:
the reaction of a compound of formula (V)

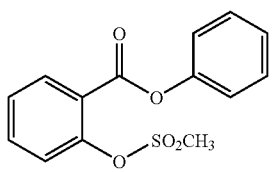

(V)

with a basic agent, as defined above, to obtain a ketosultone of formula (II), (II)

the reaction of compound (II) with hydroxylamine, and, if desired, subsequent crystallization of the product thus obtained.

The following examples further illustrate the invention.

EXAMPLE 1

Preparation of the Oxime of Formula (III)

A solution of ketosultone (II) (50.0 g; 252.5 mmol) in 150 ml of methanol is added at room temperature with hydroxylamine hydrochloride (18.0 g; 252.5 mmol). The suspension is added dropwise with triethylamine (25.5 g; 252.5 mmol) in about 1 hour. The resulting solution is stirred for 1-2 hours, then diluted with 300 ml of water. The corresponding oxime (III) precipitates, which is filtered and washed with water. (50.3 g; yield: 95%).

EXAMPLE 2

Preparation of the Oxime of Formula (III) in Crystalline Form

A solution of ketosultone (II) (50.0 g; 252.5 mmol) in 500 ml of dichloromethane is added at room temperature with hydroxylamine hydrochloride (18.0 g; 252.5 mmol). The suspension is added dropwise with triethylamine (25.5 g; 252.5 mmol) in about 1 hour. The resulting solution is stirred for 1-2 hours, then washed with 300 ml of water. The solvent is evaporated off and the residue is re-crystallized from toluene (650 ml), thereby obtaining a corresponding crystalline oxime (III) (40.2 g; yield: 76%). Relevant X-Ray Powder pattern is shown in Table 1 above.

$^1$H-NMR-300 MHz-(DMSO-$d_6$): δ 5.06 (s, 2H); 7.33 (m, 2H); 7.55 (dd, 1H); 8.0(d,1H).

Mass spectrum: E.I.- m/e: M$^+$213

EXAMPLE 3

Preparation of benzo[d]isoxazol-3-yl-methanesulfonic acid lithium salt (I)

A suspension of oxime (III) (50 g; 265.7 mmol) in 250 ml of water is added dropwise with a 2 M lithium hydroxide solution (134 ml; 265.7 mmols) in water. After reacting for 3 hours at room temperature, the solution is evaporated to residue, then added with toluene and residual humidity is azeotropically removed. The product is then filtered and dried under vacuum, thereby obtaining 48 g of benzo[d] isoxazol-3-yl-methanesulfonic acid lithium salt (Yield: 85%).

EXAMPLE 4

Preparation of the benzo[d]isoxazol-3-yl-methanesulfonic acid, sodium salt (I)

A suspension of oxime (III) (50 g; 265.7 mmol) in 250 ml of water is added dropwise with a 2 M sodium hydroxide solution (134 ml; 265.7 mmol) in water. After reacting for 3 hours at room temperature the solution is evaporated to residue, then added with toluene and residual humidity is azeotropically removed. The product is then filtered and dried under vacuum, thereby obtaining 43 g of benzo[d] isoxazol-3-yl-methanesulfonic acid sodium salt. (Yield: 70%).

EXAMPLE 5

Preparation of 2,2-dioxo-2,3-dihydro-2lambda*6*-benzo[e][1,2oxathiin-4-one: Ketosultone of Formula (II)

A solution of a mesylate (V) (5.0 g; 17.1 mmol) in 20 ml of tetrahydrofuran is added with 5.5 g (35.9 mmol) of 1,8-diazabicyclo[5,4,0]undec-4-ene. The reaction mixture is stirred for about 12 hours at room temperature (approx. 20-25° C.). The solution is then heated to 35° C. for about 2 hours, then diluted with 20 ml of water. Tetrahydrofuran is then distilled off under vacuum. Upon acidification of residue to pH<3, the product starts to crystallize. The mixture is cooled to about 0-5° C. and the product is filtered, washed with water and dried under vacuum, thereby obtaining 2.8 g of ketosultone (II) (Yield: 80%) $^1$H NMR: (CDCl$_3$): δ ppm: 4.4 ppm (s, 2H); 7.3 ppm (d, 1H); 7.4 ppm (t, 1H); 7.7 (t, 1H); 8.1 (d, 1H).

EXAMPLE 6

Preparation of 2,2-dioxo-2,3-dihydro-2lambda*6*-benzo[e],[1,2]oxathiin-4-one; Ketosultone of Formula (II)

A solution of a mesylate (V) (5.0 g; 17,1 mmol) in 20 ml of tetrahydrofuran is added with 0.5 g (3,59 mmol) of 1,8-diazabicyclo[5,4,0]undec-4-ene, 5.0 g (36.2 mmol) of potassium carbonate and 5.0 g of water. The mixture is stirred to about 30-35° C. for 10-14 hours, after that it is diluted with 20 ml of water and THF is distilled off under vacuum. Upon acidification of residue to pH<3, the product starts to crystallize. The mixture is cooled to about 0-5° C. and the product is filtered, washed with water and dried under vacuum, thereby obtaining 2.2 g of ketosultone (II). (Yield: 65%).

EXAMPLE 7

Preparation of Mesylate of Formula (V)

100 g (467 mmol) of phenyl salicylate (VI) and 54.5 g (476 mmol) of methanesulfonyl chloride are reacted in 500 ml of toluene, under stirring. The. solution is cooled to about 0-5° C. and 48.7 g (481 mmol) of triethylamine are dropped therein in about 15 minutes. The reaction temperature raises to about 37° C. Afterwards the mixture is stirred at about 20-25° C. for 10-14 hours, monitoring the reaction by NMR and/or HPLC. Finally the solution is diluted with 500 ml of water. The formed precipitate is filtered. The organic filtrate is separated and evaporated under vacuum. The residue is combined with the precipitate and dried under vacuum at 60° C. for about 3 hours, thereby obtaining 130 g of product.

$^1$H NMR: (CDCl$_3$): δ ppm: 3.3 ppm (s, 3H); 7.2 ppm (m, 3H); 7.4 ppm (m, 4H); 7.6 (t, 1H); 8.2 (d, 1H).

EXAMPLE 8

Preparation of the benzo'd]isoxazol-3-yl-methanesulfonic acid triethylammonium salt (I)

A solution of oxime (III) (50 g; 265.7 mmol) in 25 ml of methanol is added dropwise drop with triethylamine (26.7 g; 265.7 mmol) in water. After reacting for 8 hours at about 40° C., the solution is evaporated to a residue, thereby obtaining 57 g of benzo[d]isoxazol-3-yl-methanesulfonic acid triethylammonium salt (Yield: 70%).

EXAMPLE 9

Preparation of 2,2-dioxo-2,3-dihydro-2lambda*6*-benzo[e][1,2]oxathiin-4-one, Ketosultone of Formula (II)

A solution of a mesylate (V) (5.0 g; 17.1 mmol) in 20 ml of tetrahydrofuran is added with 3.45 g (35.9 mmol) of sodium tert-butoxide. The reaction mixture is stirred for about 12 hours at room temperature (approx. 20-25° C.). The solution is then heated to about 35° C. for approx. 2 hours, then diluted with 20 ml of water. Tetrahydrofuran is then distilled off under vacuum. Upon acidification of residue to pH<3, the product starts to crystallize. The mixture is cooled to about 0-5° C. and the product is filtered, washed with water and dried under vacuum, thereby obtaining 2.4 g of ketosultone (II) (Yield: 70%).

The invention claimed is:

1. A process for the preparation of benzo[d]isoxazol-3-yl-methanesulfonic acid of formula (I)

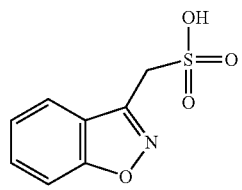

(I)

or a salt thereof, comprising the reaction of an oxime of formula (III)

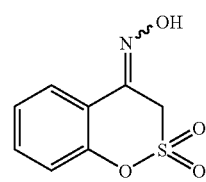

(III)

with a basic agent.

2. A process as claimed in claim 1, wherein the basic agent is an organic base or an alkali or alkaline-earth metal hydroxide.

3. A process as claimed in claim 2, wherein the basic agent is lithium, sodium, potassium, calcium or magnesium hydroxide, or a secondary or tertiary amine.

4. A process for the preparation of zonisamide, comprising the treatment of a benzo[d]isoxazol-3-yl-methanesulfonic acid of formula (I)

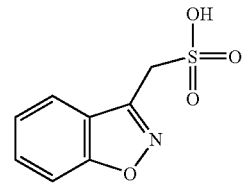

(I)

or a salt thereof with a halogenating agent to obtain a benzo[d]isoxazol-3-yl-methanesulfonyl halide of formula (IV)

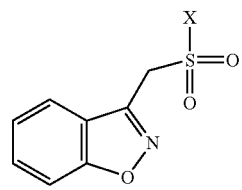

(IV)

wherein X is halogen, and the treatment of compound (IV) with ammonia; wherein the benzo[d]isoxazol-3-yl-methanesulfonic acid of formula (I), or a salt thereof, is obtained by a process comprising treating an oxime of formula (III)

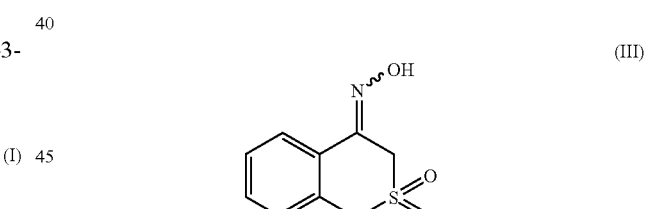

(III)

with a basic agent.

5. A process as claimed in claim 4, wherein the basic agent is an organic base or an alkali or alkaline-earth metal hydroxide.

6. A process as claimed in claim 1, wherein an oxime of formula (III), or an isomers thereof, optionally in the crystalline form, is prepared by a process comprising:

the reaction of a compound of formula (V)

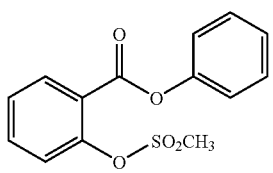

(V)

with a basic agent, to obtain a ketosultone of formula (II);

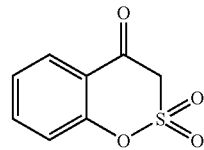
(II)

the reaction of compound (II) with hydroxylamine; and, if desired, crystallization.

7. A process for preparing a ketosultone of formula (II), i.e. 2,2-dioxo-2,3-dihydro-2lambda*6*-benzo[e][1,2]oxathiin-4-one, comprising reacting a compound of formula (V)

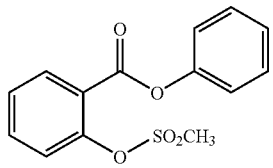
(V)

with a basic agent.

8. A process as claimed in claim 4, wherein an oxime of formula (III), or an isomers thereof, optionally in the crystalline form, is prepared by a process comprising:

the reaction of a compound of formula (V)

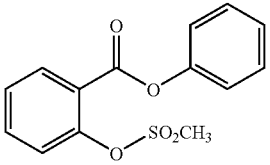
(V)

with a basic agent, to obtain a ketosultone of formula (II);

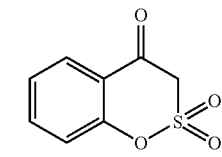
(II)

the reaction of compound (II) with hydroxylamine; and, if desired, crystallization.

* * * * *